United States Patent
Koyanagi et al.

(10) Patent No.: US 12,377,276 B2
(45) Date of Patent: Aug. 5, 2025

(54) PULSE DISCRIMINATION DEVICE AND ELECTROCARDIOGRAM ANALYZER

(71) Applicant: NIHON KOHDEN CORPORATION, Tokyo (JP)

(72) Inventors: Takashi Koyanagi, Tokorozawa (JP); Kazutora Iinuma, Tokorozawa (JP); Hiroshi Kubo, Tokorozawa (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 199 days.

(21) Appl. No.: 17/395,674

(22) Filed: Aug. 6, 2021

(65) Prior Publication Data
US 2021/0361951 A1   Nov. 25, 2021

Related U.S. Application Data

(62) Division of application No. 16/573,002, filed on Sep. 17, 2019, now Pat. No. 11,433,242.

(30) Foreign Application Priority Data

Sep. 25, 2018   (JP) .................................. 2018-179345

(51) Int. Cl.
*A61N 1/365* (2006.01)
*A61B 5/00* (2006.01)
(Continued)

(52) U.S. Cl.
CPC .......... *A61N 1/36507* (2013.01); *A61B 5/316* (2021.01); *A61B 5/33* (2021.01);
(Continued)

(58) Field of Classification Search
None
See application file for complete search history.

(56) References Cited

U.S. PATENT DOCUMENTS 3,552,386 A * 1/1971 Horth ................. A61B 5/02416
600/516
3,814,083 A   6/1974 Fletcher et al.
(Continued)

FOREIGN PATENT DOCUMENTS

JP   H04-501213 A   3/1992
JP   H06-154342 A   6/1994
(Continued)

OTHER PUBLICATIONS

United States Office Action issued in U.S. Appl. No. 16/573,088 dated May 12, 2021.
(Continued)

*Primary Examiner* — Carl H Layno
*Assistant Examiner* — Manolis Pahakis
(74) *Attorney, Agent, or Firm* — McDonald Hopkins LLC

(57) ABSTRACT

A pulse discrimination device is configured to receive electrical signals from a plurality of positions of a living body to which a pacing device for outputting a pacing pulse to cause a heart to beat is attached, and is configured to discriminate the pacing pulse included in the electrical signals. The pulse discrimination device includes a differential processor configured to calculate a difference of the electrical signals received from the plurality of positions, a sum processor configured to calculate a sum of the electrical signals received from the plurality of positions, and a pulse discrimination unit configured to discriminate the pacing pulse included in the electrical signals based on the difference obtained by the differential processor and the sum obtained by the sum processor.

2 Claims, 9 Drawing Sheets

(51) Int. Cl.
  *A61B 5/316* (2021.01)
  *A61B 5/33* (2021.01)
  *A61B 5/339* (2021.01)
(52) U.S. Cl.
  CPC ............ *A61B 5/339* (2021.01); *A61B 5/7203* (2013.01); *A61B 5/7217* (2013.01)

(56) References Cited

U.S. PATENT DOCUMENTS

| | | | |
|---|---|---|---|
| 3,878,832 A | 4/1975 | Tickner et al. | |
| 4,058,118 A * | 11/1977 | Stupay | A61B 5/02438 600/503 |
| 4,105,023 A * | 8/1978 | Marchese | A61B 5/7217 600/510 |
| 4,215,697 A | 8/1980 | Demetrescu | |
| 4,226,245 A * | 10/1980 | Bennett, Jr. | A61N 1/3708 607/27 |
| 4,432,375 A * | 2/1984 | Angel | A61N 1/365 607/6 |
| 4,519,401 A * | 5/1985 | Ko | G01L 19/148 128/903 |
| 4,527,567 A | 7/1985 | Fischler et al. | |
| 4,583,553 A | 4/1986 | Shah et al. | |
| 4,585,001 A | 4/1986 | Belt | |
| 4,603,703 A | 8/1986 | McGill et al. | |
| 4,630,204 A | 12/1986 | Mortara | |
| 4,674,508 A | 6/1987 | DeCote | |
| 4,969,467 A * | 11/1990 | Callaghan | A61N 1/3706 607/30 |
| 5,010,887 A * | 4/1991 | Thornander | A61N 1/3704 607/9 |
| 5,078,133 A | 1/1992 | Heinz et al. | |
| 5,123,419 A * | 6/1992 | Platt | A61N 1/371 600/510 |
| 5,197,467 A * | 3/1993 | Steinhaus | A61N 1/36521 607/20 |
| 5,201,808 A * | 4/1993 | Steinhaus | A61N 1/36521 607/20 |
| 5,217,021 A | 6/1993 | Steinhaus et al. | |
| 5,231,990 A | 8/1993 | Gauglitz | |
| 5,330,512 A | 7/1994 | Hauck et al. | |
| 5,331,966 A * | 7/1994 | Bennett | A61N 1/36185 128/903 |
| 5,431,170 A * | 7/1995 | Mathews | A61B 5/681 600/323 |
| 5,448,997 A * | 9/1995 | Kruse | A61N 1/3702 600/510 |
| 5,575,809 A * | 11/1996 | Sasaki | A61B 5/7203 607/62 |
| 5,692,907 A | 12/1997 | Glassel et al. | |
| 5,697,957 A * | 12/1997 | Noren | A61N 1/3712 600/509 |
| 5,709,213 A | 1/1998 | Kruse et al. | |
| 5,713,935 A * | 2/1998 | Prutchi | A61N 1/36521 607/28 |
| 5,771,898 A | 6/1998 | Marinello | |
| 5,919,141 A * | 7/1999 | Money | A61B 5/002 600/513 |
| 6,269,268 B1 * | 7/2001 | Callaghan | A61N 1/3706 607/19 |
| 6,381,493 B1 | 4/2002 | Stadler et al. | |
| 6,456,879 B1 * | 9/2002 | Weinberg | A61N 1/3712 607/30 |
| 6,477,404 B1 * | 11/2002 | Yonce | A61B 5/30 600/510 |
| 6,588,423 B1 | 7/2003 | Sinderby | |
| 6,615,082 B1 * | 9/2003 | Mandell | A61N 1/3712 607/9 |
| 6,901,286 B1 | 5/2005 | Sinderby | |
| 6,962,155 B1 | 11/2005 | Sinderby | |
| 7,336,998 B2 | 2/2008 | Yonce | |
| 7,455,643 B1 | 11/2008 | Li et al. | |
| 7,460,900 B1 | 12/2008 | Gill et al. | |
| 7,570,989 B2 | 8/2009 | Baura et al. | |
| 7,610,084 B2 | 10/2009 | Sweeney et al. | |
| 7,661,427 B2 | 2/2010 | Sinderby et al. | |
| 7,706,865 B1 | 4/2010 | Snell | |
| 8,401,627 B1 * | 3/2013 | Farazi | A61N 1/3702 607/9 |
| 8,532,774 B1 | 9/2013 | Hedberg et al. | |
| 2002/0114386 A1 * | 8/2002 | Eklof | H03L 7/1976 375/376 |
| 2003/0023176 A1 | 1/2003 | Yonce et al. | |
| 2003/0050671 A1 * | 3/2003 | Bradley | A61N 1/3712 607/27 |
| 2004/0015197 A1 | 1/2004 | Gunderson | |
| 2007/0191900 A1 * | 8/2007 | Belk | A61N 1/365 607/28 |
| 2007/0260153 A1 | 11/2007 | Ghanem et al. | |
| 2008/0033494 A1 | 2/2008 | Swerdlow | |
| 2011/0270347 A1 * | 11/2011 | Frei | A61B 5/4094 607/45 |
| 2011/0319769 A1 | 12/2011 | Hedberg et al. | |
| 2013/0022209 A1 | 1/2013 | Tomimori et al. | |
| 2014/0155772 A1 | 6/2014 | Frei et al. | |
| 2015/0190068 A1 * | 7/2015 | Cole | A61B 5/349 600/509 |
| 2015/0283387 A1 * | 10/2015 | Sun | A61N 1/3704 607/27 |
| 2015/0305642 A1 * | 10/2015 | Reinke | A61B 5/346 600/510 |
| 2016/0095526 A1 | 4/2016 | Yoshimura | |
| 2016/0206804 A1 | 7/2016 | Holmer et al. | |
| 2016/0310746 A1 * | 10/2016 | Greenhut | A61B 5/363 |
| 2017/0056664 A1 | 3/2017 | Kane et al. | |
| 2018/0049660 A1 | 2/2018 | Sato | |
| 2019/0175918 A1 | 6/2019 | Grenz et al. | |
| 2019/0183374 A1 | 6/2019 | Reinke et al. | |
| 2021/0267527 A1 | 9/2021 | Reinke et al. | |

FOREIGN PATENT DOCUMENTS

| | | |
|---|---|---|
| JP | 2007-504917 A | 3/2007 |
| JP | 2009-240623 A | 10/2009 |
| JP | 2016-073373 A | 5/2016 |
| JP | 2017-513681 A | 6/2017 |
| WO | 2005-027720 A2 | 3/2005 |
| WO | 2011-064894 A1 | 6/2011 |
| WO | 2017-192775 A1 | 11/2017 |

OTHER PUBLICATIONS

Japanese Office Action dated Apr. 26, 2022 issued in Japanese Patent Application No. 2018-179345.
Japanese Office Action dated Apr. 26, 2022 issued in Japanese Patent Application No. 2018-179346.
United States Office Action dated May 2, 2022 issued in U.S. Appl. No. 16/573,088.
United States Office Action issued in U.S. Appl. No. 16/573,088 dated Dec. 13, 2021.
United States Office Action dated Dec. 30, 2022 issued in U.S. Appl. No. 16/573,088.
United States Office Action issued in U.S. Appl. No. 16/573,002 dated Sep. 24, 2021.

* cited by examiner

PULSE DISCRIMINATION DEVICE AND ELECTROCARDIOGRAM ANALYZER

CROSS-REFERENCE TO RELATED APPLICATIONS

This is a division of U.S. patent application Ser. No. 16/573,002 filed Sep. 17, 2019, issued as U.S. Pat. No. 11,433,242 on Sep. 26, 2022, which claims the benefit of Japanese Patent Application No. 2018-179345 filed on Sep. 25, 2018, the contents of which are incorporated herein by reference.

TECHNICAL FIELD

The presently disclosed subject matter relates to a pulse discrimination device and an electrocardiogram analyzer, and particularly to a pulse discrimination device and an electrocardiogram analyzer that receive an electrical signal from a living body to which a pacing device is attached so as to discriminate a pacing pulse included in the electrical signal.

BACKGROUND

In related art, there has been proposed a pulse discrimination device that discriminates a pacing pulse that is output from a pacing device such as a pacemaker in order to cause a heart to beat. The pulse discrimination device receives an electrical signal from a living body to which a pacing device is attached and discriminates a pacing pulse included in the electrical signal. For example, a pulse discrimination device is built in an electrocardiogram analyzer such as a patient monitor and an electrocardiograph, generates an electrocardiogram based on an electrical signal received from a living body, and discriminates a pacing pulse included in the electrical signal. Thus, for example, the output timing of the pacing pulse can be displayed on the electrocardiogram, and the electrocardiogram can be analyzed in detail.

Here, the electrical signal from the living body is received via an electrode portion disposed on the living body. However, the pacing pulse may not be reliably detected depending on a position of the electrode portion with respect to the pacing device.

As a technique for reliably detecting a pacing pulse, for example, JP-A-2009-240623 proposes a pacemaker pulse detection device that improves the detection accuracy of a pacing pulse without increasing the number of electrode portions to be used. The pacemaker pulse detection device detects an electrical signal from a plurality of directions with respect to a pacemaker using three electrode portions, and thus is capable of obtaining an electrical signal having a potential difference from any one of the electrode portions, and it is possible to reliably detect a pacing pulse.

However, the electrical signal received from the living body may include a noise similar to the pacing pulse, and the pacemaker pulse detection device of JP-A-2009-240623 cannot discriminate between a pace pulse and a noise with high accuracy, and thus may detect the noise included in the electrical signal as a pacing pulse.

For example, if a pacing pulse and a noise are discriminated based only on the amplitude of the electrical signal, the noise may be erroneously detected as the pacing pulse, and it is difficult to discriminate the pacing pulse with high accuracy.

The presently disclosed subject matter has been made in order to solve such a problem of the related art, and an object thereof is to provide a pulse discrimination device and an electrocardiogram analyzer that discriminate a pacing pulse included in an electrical signal from a living body with high accuracy.

SUMMARY

A pulse discrimination device relating to a first aspect of the presently disclosed subject matter is configured to receive electrical signals from a plurality of positions of a living body to which a pacing device for outputting a pacing pulse to cause a heart to beat is attached, and is configured to discriminate the pacing pulse included in the electrical signals. The pulse discrimination device includes: a differential processor configured to calculate a difference of the electrical signals received from the plurality of positions; a sum processor configured to calculate a sum of the electrical signals received from the plurality of positions; and a pulse discrimination unit configured to discriminate the pacing pulse included in the electrical signals based on the difference obtained by the differential processor and the sum obtained by the sum processor.

A pulse discrimination device relating to a second aspect of the presently disclosed subject matter is configured to receive electrical signals from a plurality of positions of a living body to which a pacing device for outputting a pacing pulse to cause a heart to beat is attached, and is configured to discriminate the pacing pulse included in the electrical signals. The pulse discrimination device includes: a pulse width acquisition unit configured to acquire a pulse width of the electrical signals received from the plurality of positions based on variation in an intensity of the electrical signals; and a pulse discrimination unit configured to discriminate the pacing pulse included in the electrical signals based on the pulse width acquired by the pulse width acquisition unit.

An electrocardiogram analyzer relating to a third aspect of the presently disclosed subject matter includes: the above-described pulse discrimination device; an electrocardiogram generator configured to generate an electrocardiogram based on an electrical signal received from a living body; and a display configured to display the electrocardiogram generated by the electrocardiogram generator.

DESCRIPTION OF EMBODIMENTS

Hereinafter, embodiments of the presently disclosed subject matter will be described by reference to drawings.

Embodiment 1

Figure 1:
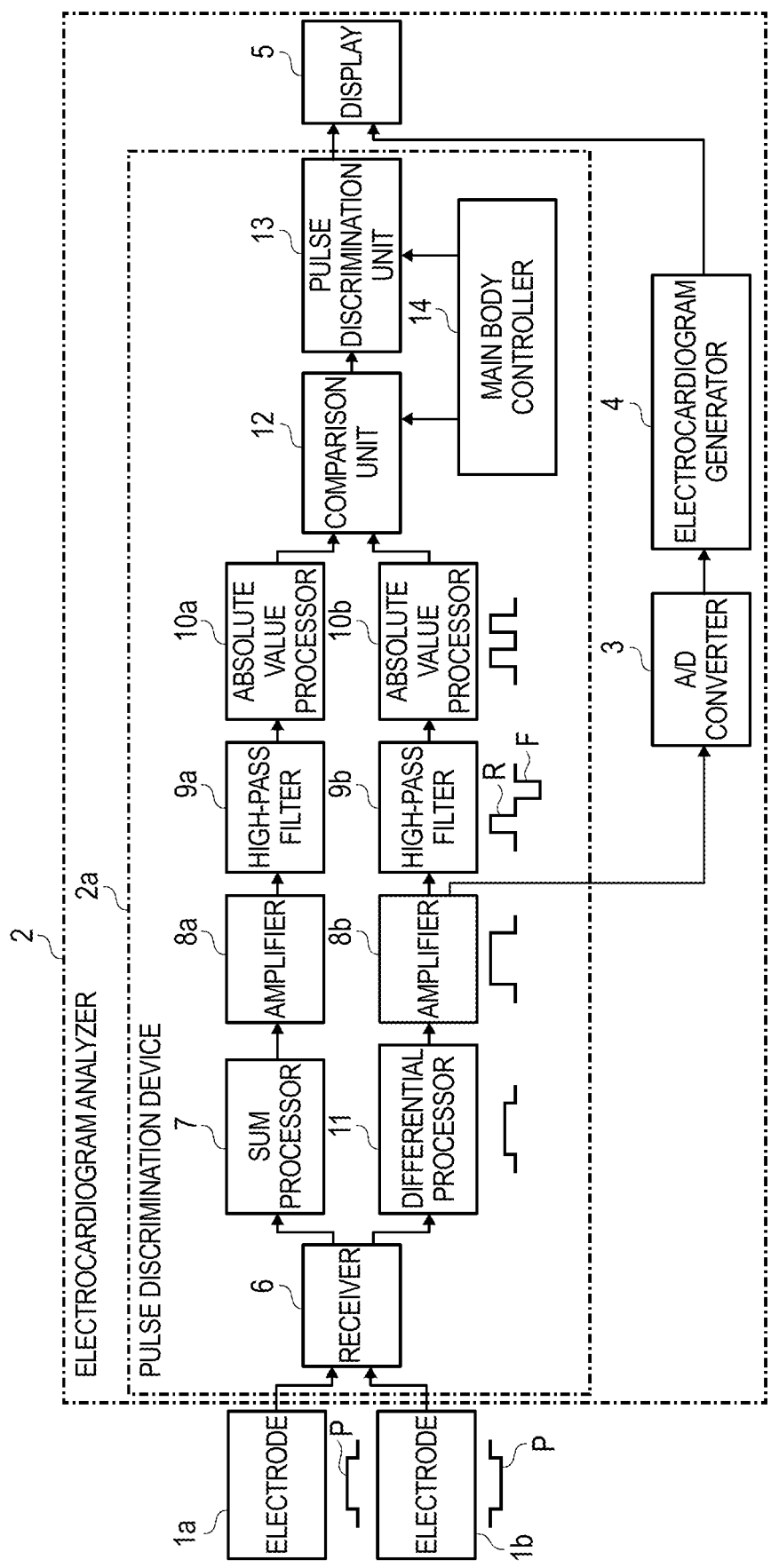
FIG. 1 is a block diagram illustrating a configuration of an electrocardiogram analyzer including a pulse discrimination device relating to Embodiment 1 of the presently disclosed subject matter.

FIG. 1 illustrates a configuration of an electrocardiogram analyzer 2 can include a pulse discrimination device relating to Embodiment 1 of the presently disclosed subject matter. The electrocardiogram analyzer 2 is connected to a pair of electrodes 1a and 1b. The electrocardiogram analyzer 2 may be, for example, an electrocardiograph for electrocardiogram measurement, or may be a patient monitor capable of acquiring other vital sign parameters (respiration, body temperature, pulse rate, blood pressure, and the like). The patient monitor may be a so-called bedside monitor or a portable device such as a medical telemeter. The electrocardiogram analyzer 2 may be configured such that a display 5 can be attached and detached, or configured to transfer various data used for display.

The electrodes 1a and 1b are respectively disposed at two positions on the living body to which a pacing device is attached, and an electrical signal from the living body is input thereto. Here, the pacing device is disposed on the living body and causes a heart to beat by sequentially outputting pacing pulses toward the heart. Therefore, the electrical signals input into the electrodes 1a and 1b include not only a signal indicating movement of the heart, but also a pacing pulse. The electrodes 1a and 1b are arranged with respect to the pacing device such that the pacing pulses P are input as differential signals, that is, the pacing pulses P input to the electrode 1a and the pacing pulses P input to the electrodes 1b are input in opposite phases.

Examples of the pacing device include a pacemaker and the like.

The electrocardiogram analyzer 2 can include a pulse discrimination device 2a, an A/D converter 3, an electrocardiogram generator 4, and a display 5.

The pulse discrimination device 2a can include a receiver 6 connected to the electrodes 1a and 1b; a sum processor 7, an amplifier 8a, a high-pass filter 9a, and an absolute value processor 10a are sequentially connected to the receiver 6; and a differential processor 11, an amplifier 8b, a high-pass filter 9b, and an absolute value processor 10b are sequentially connected to the receiver 6. The amplifier 8b is also connected to the A/D converter 3. The absolute value processors 10a and 10b are respectively connected to a comparison unit 12, and the display 5 is connected to the comparison unit 12 via the pulse discrimination unit 13. A main body controller 14 is connected to the comparison unit 12 and the pulse discrimination unit 13.

The receiver 6 receives the electrical signals input to the electrodes 1a and 1b, and the electrodes 1a and 1b are detachably connected thereto.

The sum processor 7 calculates a sum of the electrical signals received by the receiver 6 from the electrodes 1a and 1b, and may be configured with, for example, a summing amplifier circuit.

The differential processor 11 calculates a difference of the electrical signals received by the receiver 6 from the electrodes 1a and 1b, and may be configured with, for example, a differential amplifier circuit.

The amplifier 8a amplifies the intensity of the electrical signal summed by the sum processor 7. The amplifier 8b amplifies the intensity of the electrical signal differentiated by the differential processor 11. The amplification units 8a and 8b may be configured with, for example, amplifier circuits.

The high-pass filter 9a attenuates a component lower than a predetermined frequency among the electrical signal amplified by the amplifier 8a, and extracts a component having a high frequency. The high-pass filter 9b attenuates a component lower than a predetermined frequency among the electrical signal amplified by the amplifier 8b, and extracts a component having a high frequency.

The absolute value processor 10a outputs an absolute value of an electrical signal processed by the high-pass filter 9a. The absolute value processor 10b outputs an absolute value of an electrical signal processed by the high-pass filter 9b. The absolute value processors 10a and 10b may be configured with, for example, absolute value circuits.

The comparison unit 12 compares the intensity of the electrical signal output from the absolute value processor 10a with the intensity of the electrical signal output from the absolute value processor 10b, and may be configured with, for example, a comparator circuit.

The pulse discrimination unit 13 discriminates the pacing pulse P included in the electrical signal based on a comparison result of the comparison unit 12. For example, in a case where the absolute value of the difference output from the absolute value processor 10b is equal to or larger than the absolute value of the sum output from the absolute value processor 10a in the comparison result of the comparison unit 12, the pulse discrimination unit 13 determines the electrical signals received by the receiver 6 are the pacing pulse P. On the other hand, in a case where the absolute value of the difference output from the absolute value processor 10b is smaller than the absolute value of the sum output from the absolute value processor 10a in the comparison result of the comparison unit 12, the pulse discrimination unit 13 determines the electrical signals received by the receiver 6 are a noise.

The main body controller 14 controls each unit in the pulse discrimination device 2a.

The pulse discrimination unit 13 and the main body controller 14 are configured with a CPU and an operation program for causing the CPU to perform various processing, but may also be configured with digital circuits.

The A/D converter 3 is connected to the amplifier 8b, and performs analog/digital conversion on an analog electrical signal amplified by the amplifier 8b to generate a digital electrical signal.

The electrocardiogram generator 4 is connected to the A/D converter 3 and generates an electrocardiogram based on the digital electrical signal generated by the A/D converter 3.

The display 5 is connected to the electrocardiogram generator 4 and the pulse discrimination unit 13, displays the electrocardiogram generated by the electrocardiogram generator 4, and displays a pulse mark indicating output of the pacing pulse P at the position in the electrocardiogram discriminated as the pacing pulse P by the pulse discrimination unit 13.

Next, operation of Embodiment 1 will be described.

First, the electrodes 1a and 1b illustrated in FIG. 1 are arranged at two positions on the surface of the living body. The pacing device (not illustrated) is attached to the living body, and the pacing pulses P for causing the heart to beat are sequentially output from the pacing device toward the heart. Therefore, an electrical signal including the pacing pulses P is propagated to the living body, and the electrical signal is input to the electrodes 1a and 1b. Here, the electrodes 1a and 1b are arranged at positions such that the pacing pulses P are input as differential signals. When an electrical signal is respectively input to the electrodes 1a and 1b, the electrical signal is output from the electrodes 1a and 1b to the receiver 6 of the pulse discrimination device 2a.

When the electrical signal output from the electrodes 1a and 1b is received by the receiver 6, the receiver 6 outputs the electrical signal received from the electrodes 1a and 1b to the sum processor 7 and outputs the electrical signal received from the electrodes 1a and 1b to the differential processor 11.

When the electrical signal output from the receiver 6 is input to the sum processor 7, the sum processor 7 processes sum processing of the electrical signal, that is, calculates the sum of the electrical signal received at the two different positions. Therefore, the pacing pulses P input as differential signals cancels each other due to the sum processing, and the intensity thereof becomes a low value, for example, zero. On the other hand, in general, noises input as in-phase signals, for example, noises caused by vibration of an external device, are increased by each other and become a large value due to the sum processing. The electrical signal obtained via the sum processing is output from the sum processor 7 to the amplifier 8a.

The electrical signal subjected to the sum processing by the sum processor 7 is amplified by the amplifier 8a, and the component having a high frequency is extracted by the high-pass filter 9a and input to the absolute value processor 10a. Then, the electrical signal input to the absolute value processor 10a is subjected to absolute value conversion, and is output from the absolute value processor 10a to the comparison unit 12.

On the other hand, when the electrical signal output from the receiver 6 is input to the differential processor 11, the differential processor 11 processes differential processing of the electrical signal, that is, calculates the difference of the electrical signal received at the two different positions. Therefore, the pacing pulses P input as differential signals are increased by each other and become a large value due to the differential processing. On the other hand, noises input as in-phase signals are canceled by each other and become a small value. The electrical signal obtained via the differential processing is output from the differential processor 11 to the amplifier 8b.

The electrical signal subjected to the differential processing by the differential processor 11 is amplified by the amplifier 8b, and a rise R component and a fall F component are extracted by the high-pass filter 9b and input to the absolute value processor 10b. Then, the electrical signal input to the absolute value processor 10b is subjected to absolute value conversion, and is output from the absolute value processor 10b to the comparison unit 12. The electrical signal amplified by the amplifier 8b is also output from the amplifier 8b to the A/D converter 3.

Figure 2:
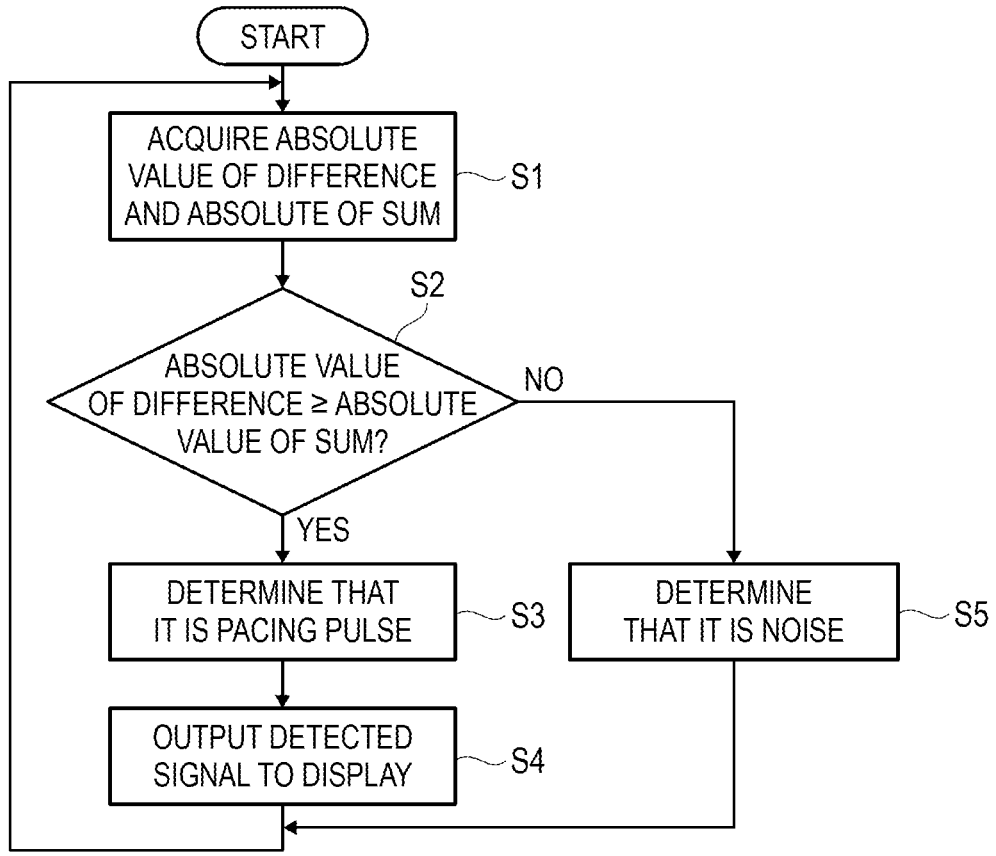
FIG. 2 is a flowchart illustrating an operation of judging a pacing pulse by a pulse discrimination unit.

In this way, the electrical signals processed by the absolute value processors 10a and 10b are input to the comparison unit 12. Thus, as illustrated in FIG. 2, in step S1, the comparison unit 12 acquires the absolute value obtained by differentiating the electrical signals and the absolute value obtained by summing the electrical signals. The comparison unit 12 compares the absolute value obtained by differentiating the electrical signals and the absolute value obtained by summing the electrical signals, and outputs the comparison result to the pulse discrimination unit 13.

When the comparison result of the comparison unit 12 is input to the pulse discrimination unit 13, in step S2, the pulse discrimination unit 13 determines whether or not the absolute value of the difference of the electrical signal is equal to or larger than the absolute value of the sum of the electrical signals.

Here, the pacing pulses P input as differential signals have an absolute value of the difference larger than a predetermined value, and have an absolute value of the sum equal to or smaller than the predetermined value. On the other hand, the noises input as in-phase signals have an absolute value of the difference equal to or smaller than the predetermined value, and have an absolute value of the sum larger than the predetermined value. That is, in a case where the pacing pulse P is input, the absolute value of the difference is equal to or larger than the absolute value of the sum, and when a noise is input, the absolute value of the difference is smaller than the absolute value of the sum.

Therefore, in a case where the absolute value of the difference of the electrical signals is equal to or larger than the absolute value of the sum of the electrical signals, in step S3, the pulse discrimination unit 13 determines that that part is the pacing pulse P. Then, in step S4, the pulse discrimination unit 13 outputs the detected signal of the pacing pulse P to the display 5. Therefore, in a case where the absolute value of the difference of the electrical signals is smaller than the absolute value of the sum of the electrical signals, in step S5, the pulse discrimination unit 13 determines that that part is a noise.

In this manner, the pulse discrimination unit 13 discriminates the pacing pulse P included in the electrical signals based on the difference of the electrical signals obtained by the differential processor 11 and the sum of the electrical signals obtained by the sum processor 7, that is, based on the characteristics of the pacing pulses P input as differential signals, and thus can discriminates the pacing pulses P with high accuracy.

In this way, when the pulse discrimination unit 13 has discriminated the pacing pulse P, the process returns to step S1, and discrimination of the pacing pulse P is repeatedly performed on the sequentially input electrical signals.

Here, the electrical signal output from the amplifier 8b to the A/D converter 3 is converted into a digital electrical signal by the A/D converter 3 and then output to the electrocardiogram generator 4. Then, the electrocardiogram generator 4 generates an electrocardiogram based on the electrical signal input from the A/D converter 3, and outputs the electrocardiogram signal to the display 5.

Figure 3:
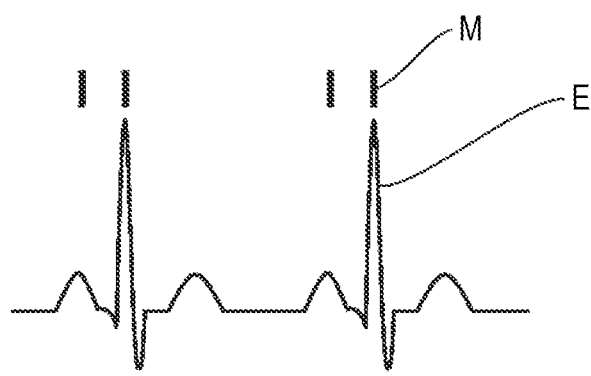
FIG. 3 is a diagram illustrating a state in which an electrocardiogram is displayed on a display.

Thereby, as illustrated in FIG. 3, an electrocardiogram E indicating beats of the heart of the living body is displayed on the display 5. In step S4, the detected signal of the pacing pulse P output from the pulse discrimination unit 13 is input to the display 5. Therefore, the display 5 displays a pulse mark M indicating output of the pacing pulse P from the pacing device in a manner superimposing the electrocardiogram E at a position corresponding to detection of the pacing pulse P.

In this way, by displaying the pulse mark M in a manner superimposing the electrocardiogram E, for example, the output timing of the pacing pulse P from the pacing device can be easily grasped, and the electrocardiogram E can be analyzed in detail.

According to the present embodiment, the pulse discrimination unit 13 discriminates the pacing pulse P included in the electrical signals based on the difference of the electrical signals obtained by the differential processor 11 and the sum of the electrical signals obtained by the sum processor 7, and thus can discriminates the pacing pulses P with high accuracy.

Embodiment 2

In Embodiment 1, the comparison unit 12 preferably compares a peak value of the absolute value obtained by differentiating the electrical signals with a peak value of the absolute value obtained by summing the electrical signals.

Figure 4:
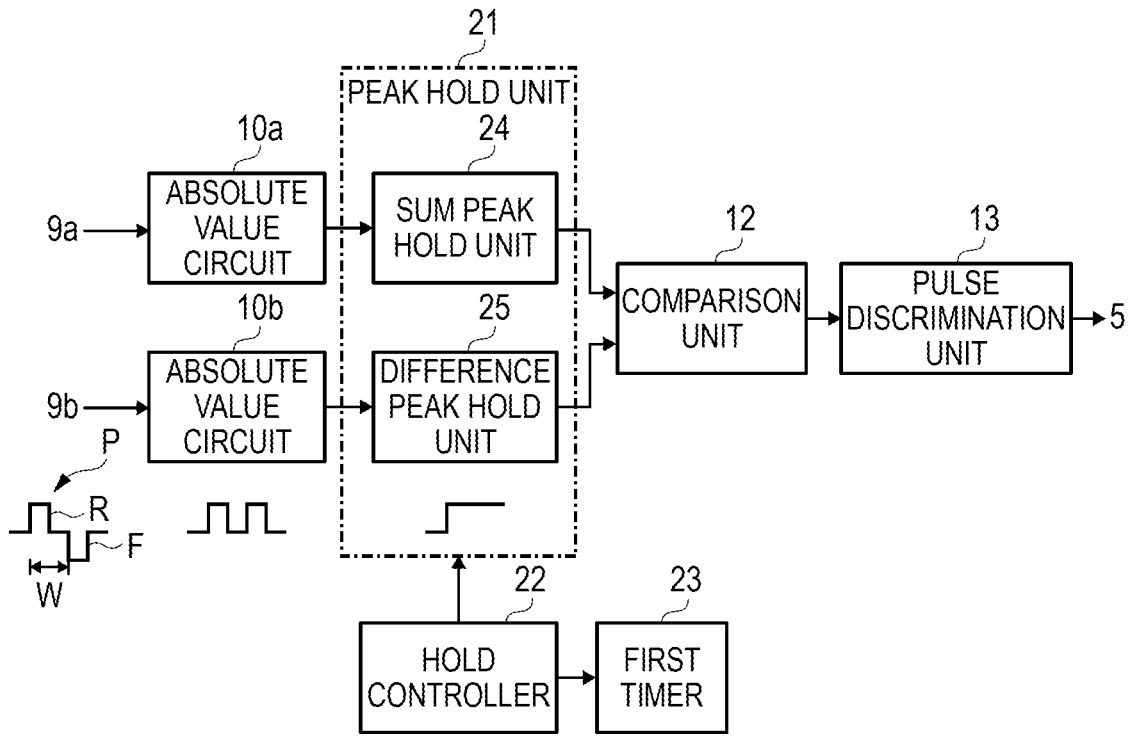
FIG. 4 is a block diagram illustrating a main part of a pulse discrimination device relating to Embodiment 2.

For example, as illustrated in FIG. 4, in Embodiment 1, a peak hold unit 21 may be connected between the absolute value processors 10a, 10b and the comparison unit 12, and a hold controller 22 and a first timer 23 may be sequentially connected to the peak hold unit 21.

The peak hold unit 21 can include a sum peak hold unit 24 and a difference peak hold unit 25.

The sum peak hold unit 24 is connected between the absolute value processor 10a and the comparison unit 12, and holds the peak value of the electrical signal output from the absolute value processor 10a, that is, the peak value of the absolute value with respect to the sum obtained by the sum processor 7, as a sum peak value.

The difference peak hold unit 25 is connected between the absolute value processor 10b and the comparison unit 12, and holds the peak value of the electrical signal output from the absolute value processor 10b, that is, the peak value of the absolute value with respect to the difference obtained by the differential processor 11, as a difference peak value.

The first timer 23 measures a hold time of the sum peak value held by the sum peak hold unit 24 and the difference peak value held by the difference peak hold unit 25.

The hold controller 22 controls the sum peak hold unit 24 and the difference peak hold unit 25 based on the hold time of the first timer 23. Specifically, in a case where the hold time of the first timer 23 reaches a predetermined pulse time, the hold controller 22 clears the sum peak value of the sum peak hold unit 24 and the difference peak value of the difference peak hold unit 25 back to zero, and performs control so as to repeatedly hold the sum peak value and the difference peak value.

Here, the pulse time is preset based on a pulse width W between the rise R and the fall F of the pacing pulse P, and is preferably determined as a value larger than the pulse width W of the pacing pulse P. For example, the pulse time may be set to a value that is larger than the pulse width W of the pacing pulse P and smaller than a time interval at which the pacing pulse P is output from the pacing device. For example, the pulse time may be set to 8 ms.

Next, operation of Embodiment 2 will be described.

First, the same as or similarly to Embodiment 1, the electrical signals input from the electrodes 1a and 1b are input to the absolute value processor 10a via the sum processor 7, the amplifier 8a, and the high-pass filter 9a, and are input to the absolute value processor 10b via the differential processor 11, the amplifier 8b, and the high-pass filter 9b.

Then, the electrical signal input to the absolute value processor 10a is subjected to absolute value conversion by the absolute value processor 10a, and then input to the sum peak hold unit 24 to hold the sum peak value. The same or similarly, the electrical signal input to the absolute value processor 10b is subjected to absolute value conversion by the absolute value processor 10b, and then input to the difference peak hold unit 25 to hold the difference peak value. At this time, the hold controller 22 starts the first timer 23 to measure the hold time of the sum peak hold unit 24 and the difference peak hold unit 25.

Here, for example, in a case where the pacing pulse P, which is differential signals, is input from the electrodes 1a and 1b, the difference peak value is held at a value larger than the predetermined value, and the sum peak value is held at a value equal to or smaller than the predetermined value. On the other hand, in a case where a noise, which is in-phase signals, is input from the electrodes 1a and 1b, the difference peak value is held at a value equal to or smaller than the predetermined value, and the sum peak value is held at a value larger than the predetermined value.

In this way, since the sum peak hold unit 24 holds the sum peak value, and the difference peak hold unit 25 holds the difference peak value, the sum peak value and the difference peak value can be easily acquired.

Therefore, in a case where the difference peak value is not held at a value larger than the predetermined value and the hold time of the first timer 23 reaches the predetermined pulse time, the hold controller 22 determines that the pacing pulse P is not detected, i.e., the signal is a noise, clears the sum peak value of the sum peak hold unit 24 and the difference peak value of the difference peak hold unit 25 back to zero, and clears the hold time of the first timer 23 back to zero. Then, the hold controller 22 restarts the first timer 23.

On the other hand, in a case where the difference peak value is held at a value larger than the predetermined value and the sum peak hold unit is held at a value equal to or smaller than the predetermined value before the hold time of the first timer 23 reaches the pulse time, the hold controller 22 outputs the sum peak value of the sum peak hold unit 24 and the difference peak value of the difference peak hold unit 25 to the comparison unit 12.

In this way, since the hold controller 22 repeatedly controls the sum peak hold unit 24 and the difference peak hold unit 25 based on the hold time of the first timer 23, it is possible to sequentially acquire the sum peak value and the difference peak value while easily removing a noise.

Subsequently, when the sum peak value of the sum peak hold unit 24 and the difference peak value of the difference peak hold unit 25 are input to the comparison unit 12, the comparison unit 12 compares the sum peak value with the difference peak value. At this time, the comparison unit 12 compares the sum peak value held by the sum peak hold unit 24 with the difference peak value held by the difference peak hold unit 25, that is, compares the values with the highest intensity, so that the difference between the values can be compared with high accuracy.

The comparison unit 12 outputs the comparison result to the pulse discrimination unit 13, and the pulse discrimination unit 13 determines whether or not the difference peak value is equal to or larger than the sum peak value from the comparison result. The same as or similarly to Embodiment 1, in a case where the difference peak value is equal to or larger than the sum peak value, the pulse discrimination unit 13 determines that that part is the pacing pulse P. On the other hand, in a case where the difference peak value is smaller than the sum peak value, the pulse discrimination unit 13 determines that that part is a noise.

According to the present embodiment, since the pulse discrimination unit 13 compares the difference peak value held by the difference peak hold unit 25 with the sum peak value held by the sum peak hold unit 24, it is possible to discriminate the pacing pulse P with high accuracy.

Embodiment 3

In Embodiments 1 and 2, a pulse detector configured to detect an electrical pulse included in an electrical signal is preferably newly arranged.

Figure 5:
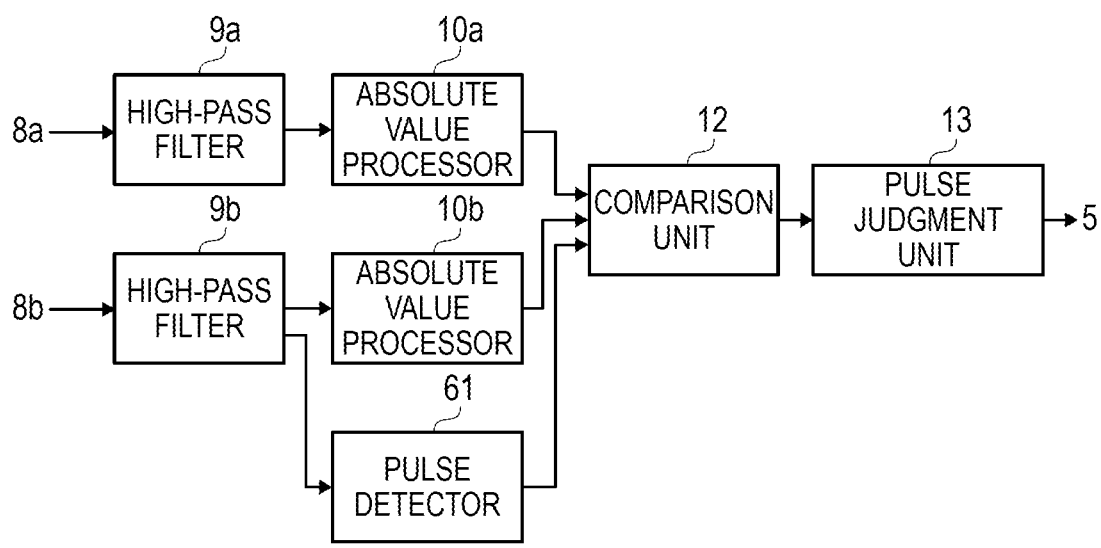
FIG. 5 is a block diagram illustrating a main part of a pulse discrimination device relating to Embodiment 3.

For example, as illustrated in FIG. 5, in Embodiment 1, a pulse detector 61 may be newly connected between the high-pass filter 9b and the pulse discrimination unit 13. The pulse detector 61 detects an electrical pulse included in an electrical signal input from the high-pass filter 9b based on variation in an intensity of the electrical signal. Specifically, in a case where the variation in the intensity of the electrical signal exceeds a preset threshold, the pulse detector 61 detects the signal as an electrical pulse. Here, the electrical pulse is a generic term for all pulses included in the electrical signal, and includes pacing pulses and noise pulses. The noise pulse corresponds to, for example, an in-phase noise and a continuous pulse.

Figure 6:
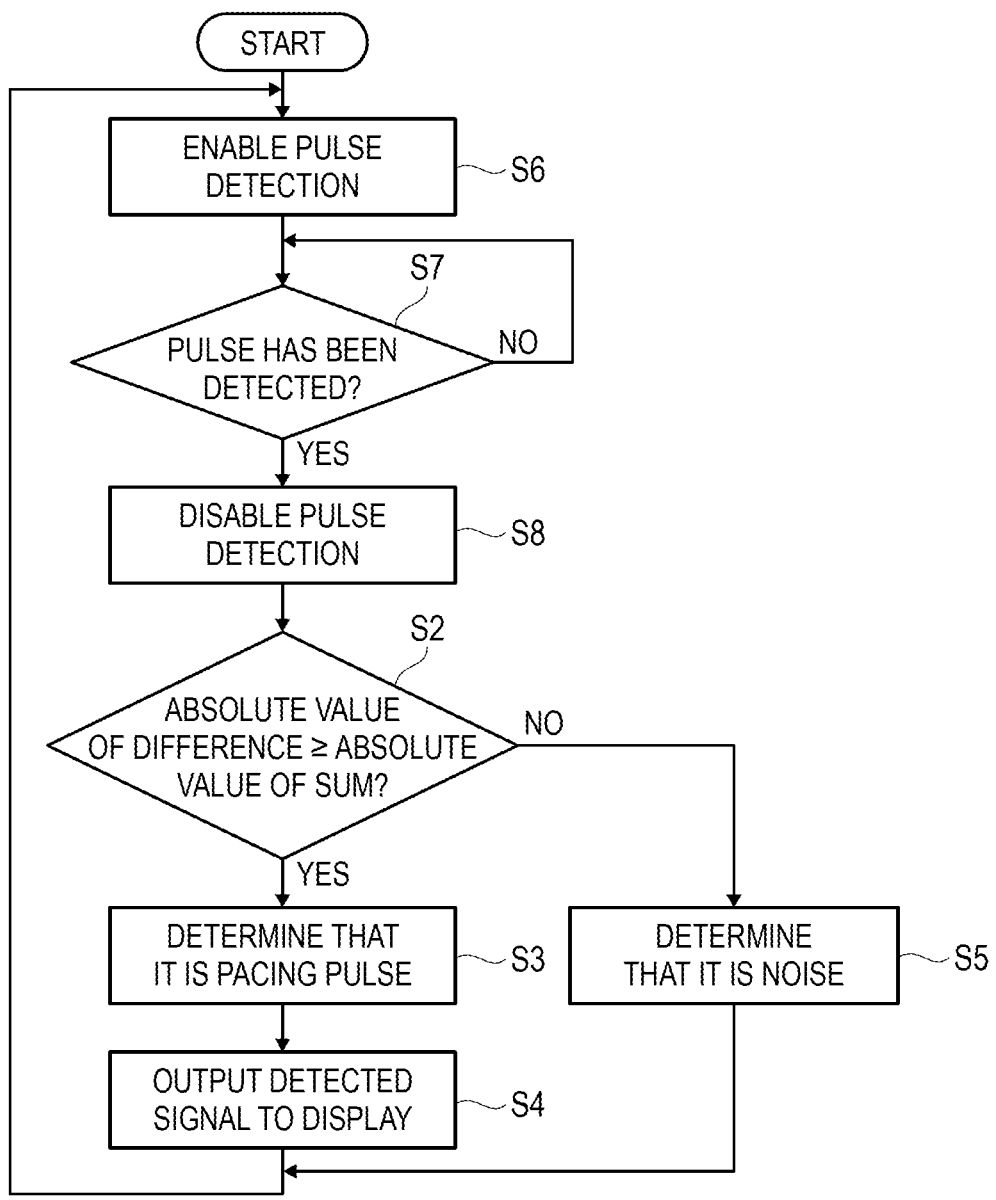
FIG. 6 is a flowchart illustrating an operation of Embodiment 3.

Next, operation of Embodiment 3 will be described with reference to the flowchart of FIG. 6.

First, in step S6, pulse detection by the pulse detector 61 is enabled. Subsequently, the same as or similarly to Embodiment 1, electrical signals from the living body are received by the receiver 6 via the electrodes 1a and 1b, and then input to the comparison unit 12 via the sum processor 7, the amplifier 8a, the high-pass filter 9a, and the absolute value processor 10a, and are input to the comparison unit 12 via the differential processor 11, the amplifier 8b, the high-pass filter 9b, and the absolute value processor 10b. An electrical signal processed by the high-pass filter 9b is also input to the pulse detector 61.

The pulse detector 61 detects an electrical pulse included in the electrical signal input from the high-pass filter 9b based on the variation in the intensity of the electrical signal. In a case where an electrical pulse is detected in step S7, the pulse detector 61 outputs the detected signal of the electrical pulse to the comparison unit 12, and disables the pulse detection in step S8. On the other hand, in a case where no electrical pulse is detected, the pulse detector 61 repeats step S7 until an electrical pulse is detected.

In this way, when the electrical signals processed by the absolute value processors 10a and 10b and the detected signal of the electrical pulse detected by the pulse detector 61 are input to the comparison unit 12, the comparison unit 12 compares the absolute values of the difference and the absolute value of the sum corresponding to the electrical pulse detected by the pulse detector 61, and outputs the comparison result to the pulse discrimination unit 13. Subsequently, the pulse discrimination unit 13 determines in step S2 the same as or similarly to Embodiment 1. The pulse discrimination unit 13 proceeds to step S3 to determine that the electrical pulse is the pacing pulse P in a case where it is determined that the absolute value of the difference is equal to or larger than the absolute value of the sum, and proceeds to step S5 to determine that the electrical pulse is a noise in a case where it is determined that the absolute value of the difference is smaller than the absolute value of the sum.

According to the present embodiment, the pulse discrimination unit 13 determines whether or not the absolute value of the difference is equal to or larger than the absolute value of the sum with respect to the electrical pulse detected by the pulse detector 61, and thus can discriminate the pacing pulse P included in the electrical signals with higher accuracy.

Embodiment 4

In the above-described Embodiments 1 to 3, the pulse discrimination unit 13 discriminates the pacing pulse P included in the electrical signals based on the difference obtained by the differential processor 11 and the sum obtained by the sum processor 7, but may also discriminate based on the pulse width W of the pacing pulse P.

Figure 7:
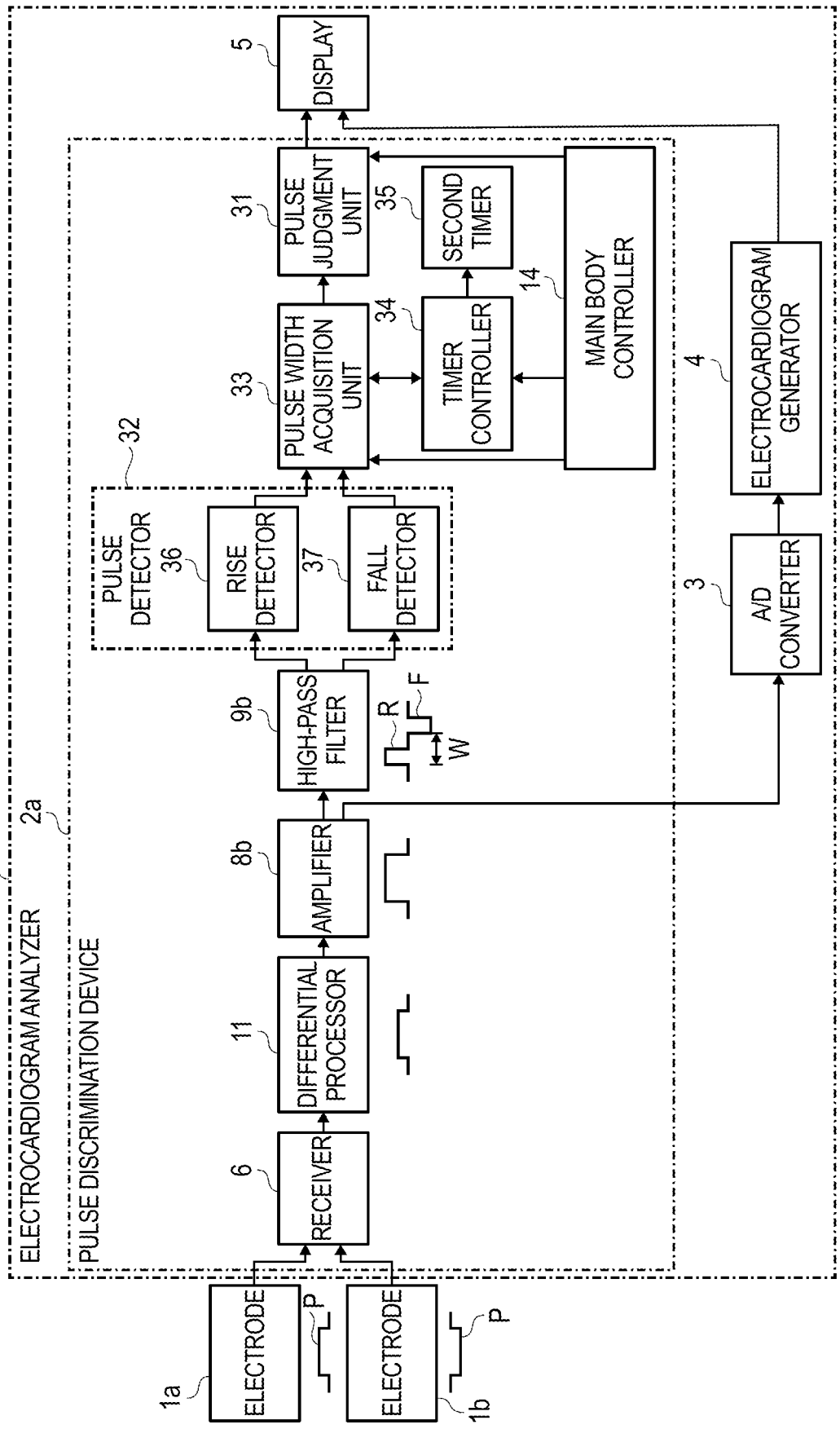
FIG. 7 is a block diagram illustrating a configuration of an electrocardiogram analyzer including a pulse discrimination device relating to Embodiment 4 of the presently disclosed subject matter.

For example, as illustrated in FIG. 7, the sum processor 7, the amplifier 8a, the high-pass filter 9a, the absolute value processor 10a, the absolute value processor 10b, and the comparison unit 12 in Embodiment 1 are excluded, and a pulse discrimination unit 31 is disposed instead of the pulse discrimination unit 13. A pulse detector 32 and a pulse width acquisition unit 33 are sequentially connected between the high-pass filter 9b and the pulse discrimination unit 31, a timer controller 34 and a second timer 35 are sequentially connected to the pulse width acquisition unit 33, and the main body controller 14 is connected to the pulse width acquisition unit 33 and the pulse discrimination unit 31.

The pulse detector 32 detects the rise R and the fall F of the electrical signals received from the electrodes 1a and 1b arranged at two positions of the living body, and can include a rise detector 36 and a fall detector 37.

The rise detector 36 is connected between the high-pass filter 9b and the pulse width acquisition unit 33, receives the electrical signal obtained by extracting the rise R component and the fall F component in the high-pass filter 9b, and detects the rise R based on the variation in the intensity of the electrical signal.

The fall detector 37 is connected between the high-pass filter 9b and the pulse width acquisition unit 33, receives the electrical signal obtained by extracting the rise R component and the fall F component in the high-pass filter 9b, and detects the fall F based on the variation in the intensity of the electrical signal.

The second timer 35 measures a time between a time of the rise R detected by the rise detector 36 and a time of the fall F detected by the fall detector 37.

The timer controller 34 controls the second timer 35 in accordance with detection of the rise R and the fall F in the pulse detector 32. Specifically, the timer controller 34 start measurement of the second timer 35 when one of the rise R and the fall F is detected in the pulse detector 32, and to stop and clear the measurement of the second timer 32 when the other one of the rise R and the fall F is detected in the pulse detector 32. Further, the timer controller 34 stops and clears the second timer 35 in a case where a measurement time of the second timer 35 reaches a predetermined pulse time after the one of the rise R and the fall F is detected and before the other one is detected in the pulse detector 32.

The pulse width acquisition unit 33 acquires the pulse width W between one fall F and another fall F based on the time measured by the second timer 35.

The same as or similarly to Embodiment 2, the pulse time is preset based on the pulse width W of the pacing pulse P, and may be determined as, for example, 8 ms, which is a value larger than the pulse width W of the pacing pulse P.

Figure 8:
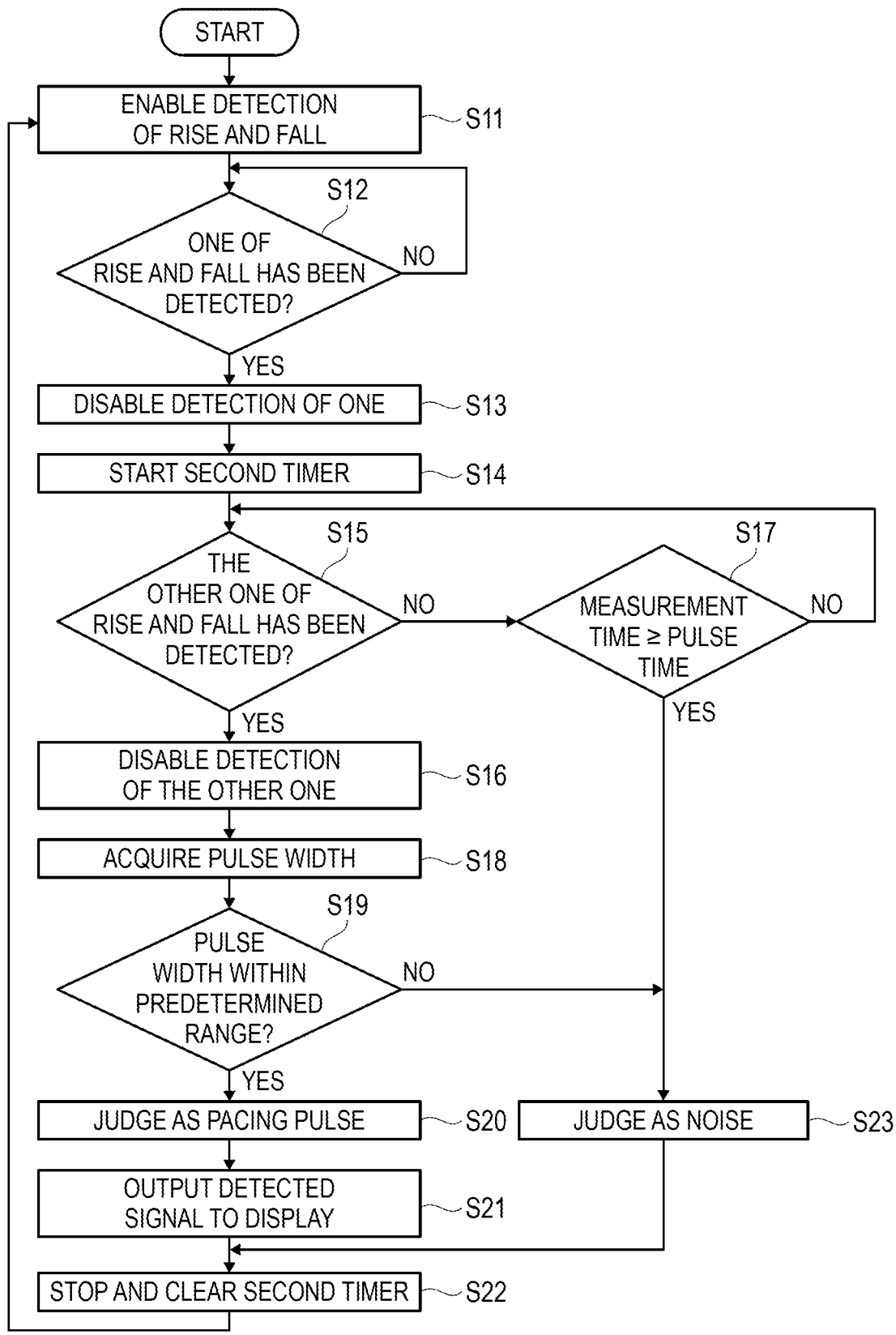
FIG. 8 is a flowchart illustrating an operation of Embodiment 4.

Next, operation of Embodiment 4 will be described with reference to the flowchart of FIG. 8.

First, in step S11, detection of the rise R in the rise detector 36 is enabled, and detection of the fall F in the fall detector 37 is enabled. The same as or similarly to Embodiment 1, the electrical signals from the living body are respectively output to the rise detector 36 and the fall detector 37 of the pulse detector 32 via the electrodes 1a and 1b, the receiver 6, the differential processor 11, the amplifier 8b, and the high-pass filter 9b.

When the electrical signal is input to the rise detector 36, the rise detector 36 detects the rise R of the electrical pulse based on the variation in the intensity of the electrical signal.

The same or similarly, when the electrical signal is input to the fall detector 37, the fall detector 37 detects the fall F of the electrical pulse based on the variation in the intensity of the electrical signal. In a case where the rise R is detected in the rise detector 36, the detected signal is output to the pulse width acquisition unit 33, and in a case where the fall F is detected in the fall detector 37, the detected signal is output to the pulse width acquisition unit 33.

Then, in step S12, the pulse width acquisition unit 33 repeatedly determines whether or not one of the rise R and the fall F is detected. Here, for example, in a case where the detected signal is input from the rise detector 36 to the pulse width acquisition unit 33, the pulse width acquisition unit 33 determines that the rise R is detected as one of the rise R and the fall F, and disables detection of the rise R by the rise detector 36 in Step S13. In addition, the timer controller 34 starts the second timer 35 in step S14.

Subsequently, when the detected signal is input from the fall detector 37 to the pulse width acquisition unit 33, the pulse width acquisition unit 33 determines that the fall F is detected as the other of the rise R and the fall F in step S15, and proceeds to step S16. On the other hand, in a case where no detected signal is input from the fall detector 37 to the pulse width acquisition unit 33, the pulse width acquisition unit 33 determines that the fall F is not detected, and proceeds to step S17.

When the process proceeds to step S16, the pulse width acquisition unit 33 disables detection of the falling F by the fall detector 37, and in step S18, acquires the measurement time of the second timer 35 when the falling F is detected, that is, the pulse width W between the rise R and the fall F, via the timer controller 34.

In this way, the pulse width acquisition unit 33 can easily acquire the pulse width W between the rise R and the fall F only by measuring the detection times of the rise R and the fall F with the second timer 35 via the timer controller 34. The pulse width W thus acquired is output from the pulse width acquisition unit 33 to the pulse discrimination unit 31.

When the pulse width W is input from the pulse width acquisition unit 33 to the pulse discrimination unit 31, the pulse discrimination unit 31 determines whether or not the pulse width W is within a predetermined range in step S19. Here, the predetermined range is preset based on the pulse width W of the pacing pulse P. In general, the pulse width W of the pacing pulse P tends to fall within a range of from 0.2 ms to 3 ms, and for example, the predetermined range may be set to from 0.2 ms to 3 ms.

In a case where the pulse width W is within the predetermined range, the process proceeds to step S20, and the pulse discrimination unit 31 determines that the electrical pulse is the pacing pulse P. On the other hand, in a case where it is determined that the pulse width W is not within the predetermined range, the process proceeds to step S23, and the pulse discrimination unit 31 determines that the electrical pulse is a noise.

In this way, the pulse discrimination unit 31 discriminates the pacing pulse P included in the electrical signals based on the pulse width W, and thus can discriminate the pacing pulses P with high accuracy.

When the pacing pulse P is detected in step S20, the pulse discrimination unit 31 proceeds to step S21, and outputs the detected signal of the pacing pulse P to the display 5. Then, in step S22, the timer controller 34 stops and clears the second timer 35.

On the other hand, when the process proceeds to step S17, the pulse width acquisition unit 33 determines whether or not the measurement time of the second timer 35 is equal to or larger than the predetermined pulse time. In a case where the pulse width acquisition unit 33 determines that the measurement time of the second timer 35 is equal to or larger than the pulse time, the pulse width acquisition unit 33 outputs the determination result to the pulse discrimination unit 31, and in step S23, the pulse discrimination unit 31 determines that the electrical pulse is a noise. In a case where the measurement time of the second timer 35 is smaller than the pulse time, the pulse width acquisition unit 33 returns to step S15 to repeatedly determine whether or not the fall F is detected.

In this way, when the pulse discrimination unit 31 determines in step S23 that the electrical pulse is a noise, the process proceeds to step S22, and the timer controller 34 stops and clears the second timer 35.

When the timer controller 34 clears the second timer 35, the process returns to step S11, detection of the rising R and the falling F is enabled again, and the rise R and the fall F are repeatedly detected with respect to the sequentially input electrical signals.

According to the present embodiment, the pulse discrimination unit 31 discriminates the pacing pulse P included in the electrical signals based on the pulse width W, and thus can discriminate the pacing pulses P with high accuracy.

Embodiment 5

In Embodiment 4, after the pulse discrimination unit 31 determines that the electrical pulse included in the electrical signal is the pacing pulse P in step S20, detection of the rise R and the fall F is preferably stopped until just before the next pacing pulse P is input from the electrodes 1*a* and 1*b*.

Figure 9:
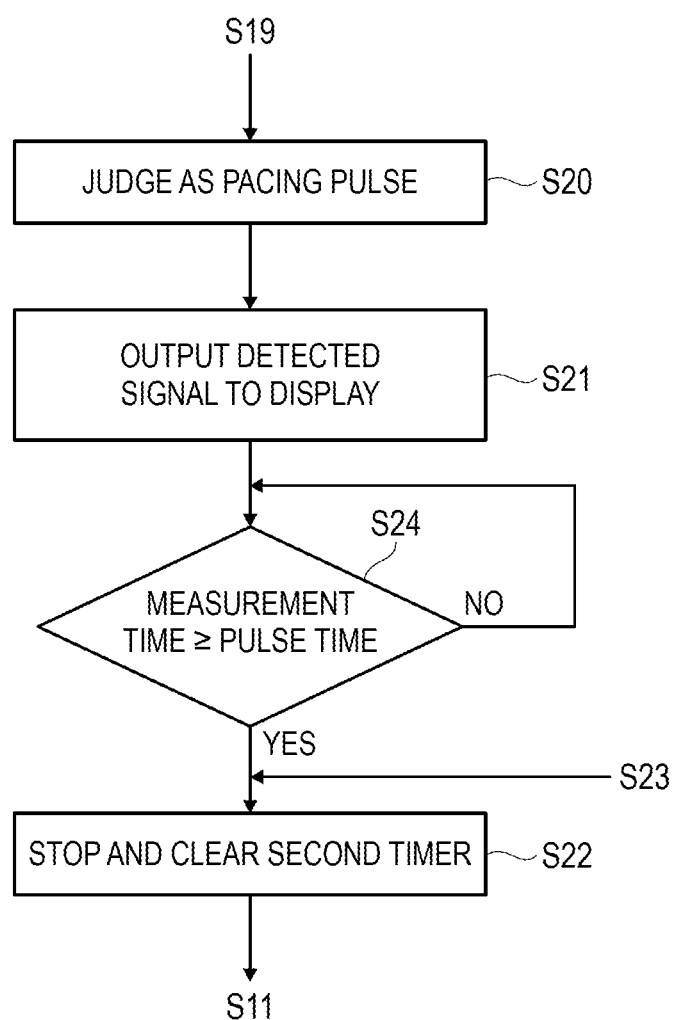
FIG. 9 is a flowchart illustrating an operation of Embodiment 5.

For example, as illustrated in FIG. 9, after the pulse discrimination unit 31 determines in step S20 of Embodiment 4 that the electrical pulse included in the electrical signal is the pacing pulse P and the detected signal of the pacing pulse P is output to the display 5 in step S21, the process proceeds to step S24. The pulse width acquisition unit 33 determines whether or not the measurement time of the second timer 35 is equal to or larger than the predetermined pulse time.

Here, the same as or similarly to Embodiment 2, the pulse time is preset based on a pulse width W of the pacing pulse P, and may be determined as, for example, 8 ms, which is a value larger than the pulse width W of the pacing pulse P, and smaller than the time interval at which the pacing pulse P is output from the pacing device.

When the pulse width acquisition unit 33 determines that the measurement time of the second timer 35 is equal to or larger than the pulse time, the pulse width acquisition unit 33 proceeds to step S22 to stop and clear the second timer via the timer controller 34. On the other hand, in a case where the pulse width acquisition unit 33 determines that the measurement time of the second timer 35 is smaller than the pulse time, the pulse width acquisition unit 33 repeats step S24 until the measurement time of the second timer 35 becomes equal to or larger than the pulse time.

In this way, since after the pacing pulse P is detected, detection of the rise R and the fall F is stopped until just before the next pacing pulse P is input to the electrodes 1*a* and 1*b*, it is possible to eliminate a noise input until the next pacing pulse P is detected, thereby preventing detection of a noise.

According to the present embodiment, after it is determined that the electrical pulse included in the electrical signal is the pacing pulse P, the pulse width acquisition unit 33 stops detection of the rise R and the fall F until just before the next pacing pulse P is input from the electrodes 1a and 1b, and thus it is possible to prevent detection of a noise.

Embodiment 6

In the above-described Embodiments 1 to 3, the pacing pulse P is discriminated based on the difference and the sum, and in Embodiments 4 and 5, the pacing pulse P is discriminated based on the pulse width W. However, the pacing pulse P included in the electrical signal may also be discriminated by combining Embodiments 1 to 3 and Embodiments 4 and 5.

Figure 10:
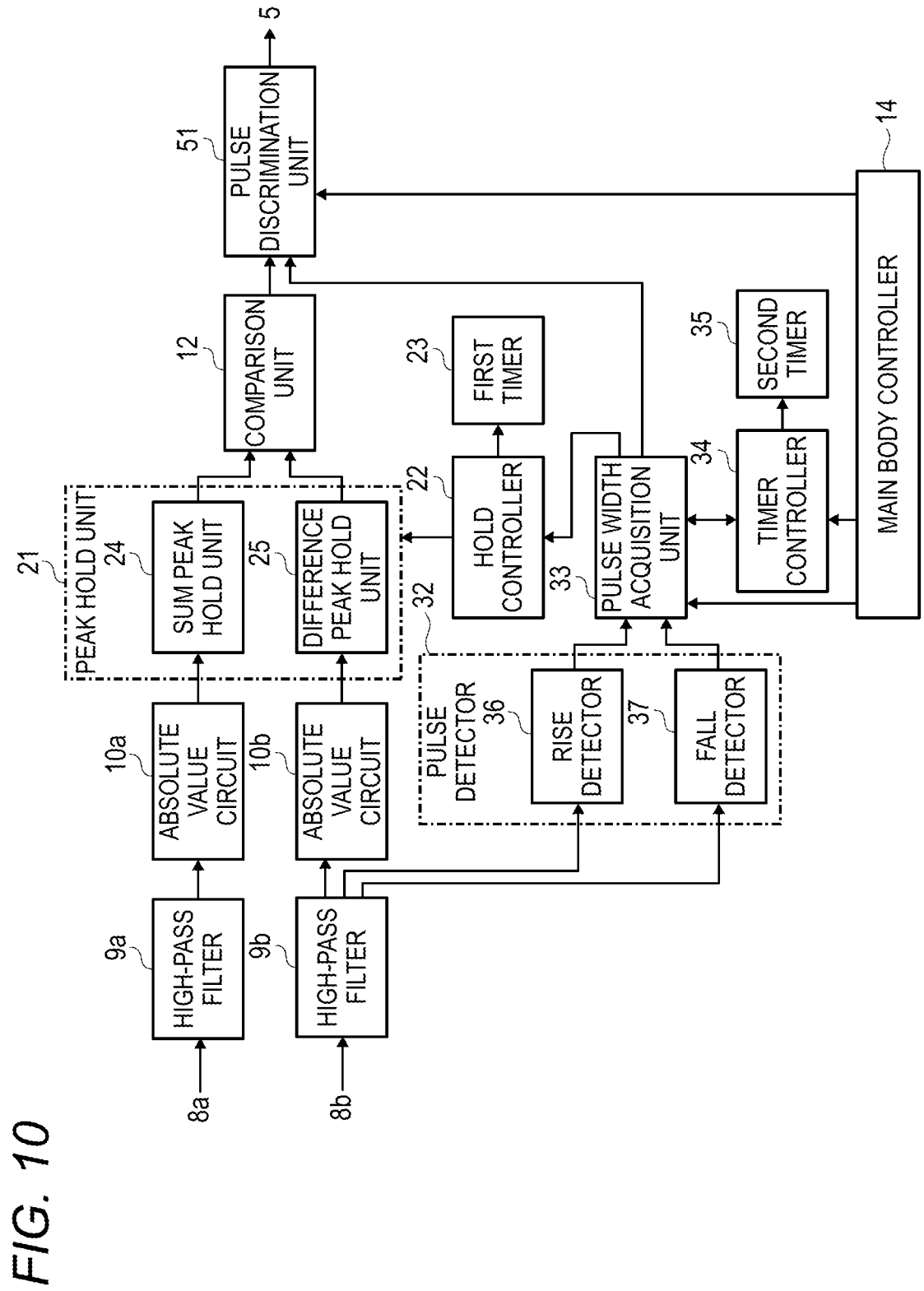
FIG. 10 is a block diagram illustrating a main part of a pulse discrimination device relating to Embodiment 6.

For example, as illustrated in FIG. 10, a pulse discrimination unit 51 is disposed instead of the pulse discrimination unit 13 in Embodiment 2, the pulse detector 32 and the pulse width acquisition unit 33 of Embodiment 4 are sequentially connected to the high-pass filter 9b, and the pulse width acquisition unit 33 is connected to the pulse discrimination unit 51. The timer controller 34 and the second timer 35 of Embodiment 4 are sequentially connected to the pulse width acquisition unit 33, and the main body controller 14 is connected to the pulse width acquisition unit 33, the timer controller 34, and the pulse discrimination unit 51. Further, the pulse width acquisition unit 33 is connected to the hold controller 22.

The pulse discrimination unit 51 discriminates the pacing pulse P included in the electrical signal based on the pulse width W acquired by the pulse width acquisition unit 33, and further discriminates the pacing pulse P based on the difference obtained by the differential processor 11 and the sum obtained by the sum processor 7.

Figure 11:
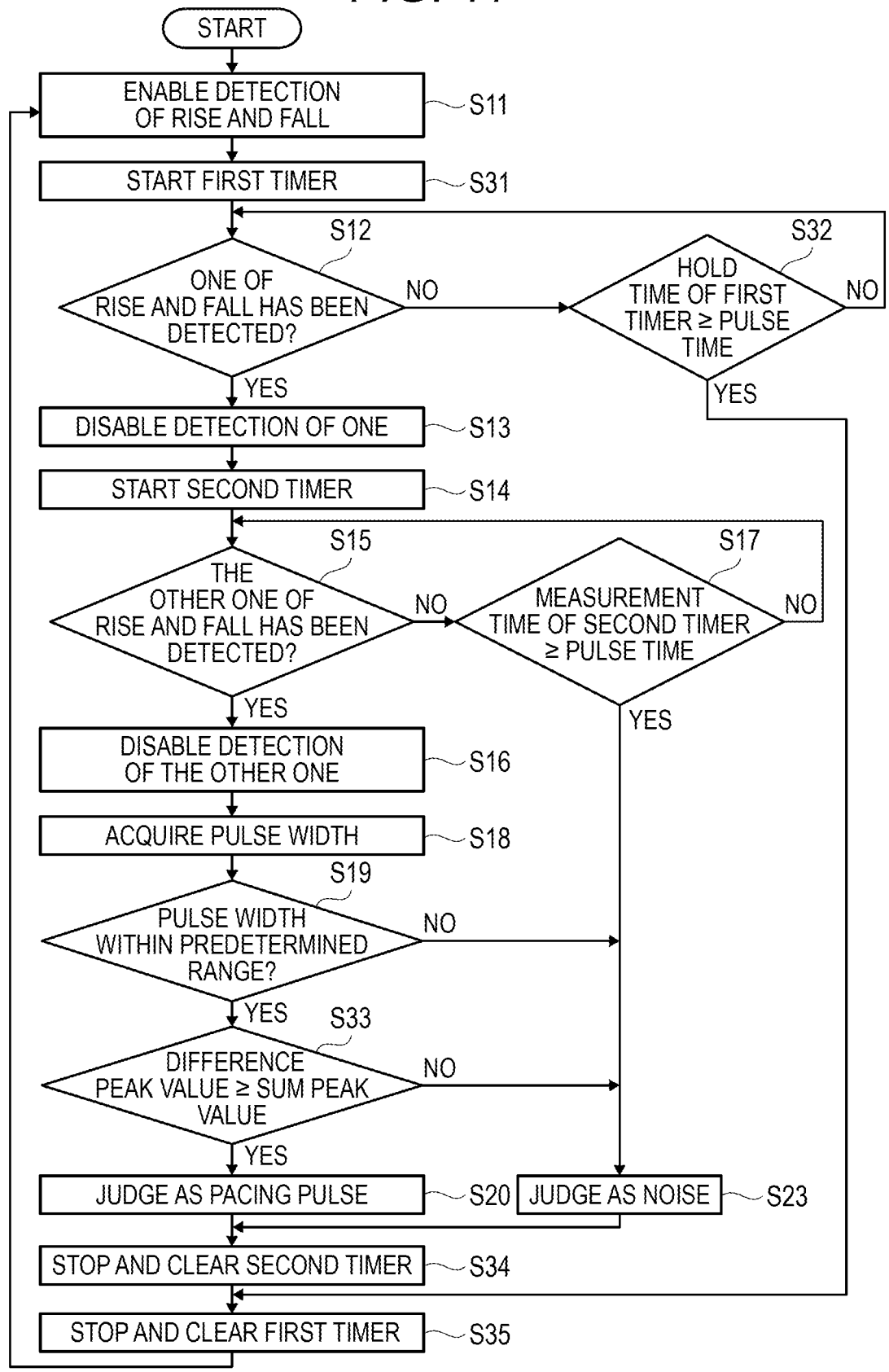
FIG. 11 is a flowchart illustrating an operation of Embodiment 6.

Next, operation of Embodiment 6 will be described with reference to the flowchart of FIG. 11.

First, the same as or similarly to Embodiment 4, in step S11, detection of the rise R in the rise detector 36 is enabled, and detection of the fall F in the fall detector 37 is enabled. In step S31, the hold controller 22 starts the first timer 23 to measure the hold time of the sum peak hold unit 24 and the difference peak hold unit 25.

The electrical signals input from the electrodes 1a and 1b are input to the sum peak hold unit 24 via the sum processor 7, the amplifier 8a, the high-pass filter 9a, and the absolute value processor 10a, and are input to the difference peak hold unit 25 via the differential processor 11, the amplifier 8b, the high-pass filter 9b, and the absolute value processor 10b. Thereby, the sum peak hold unit 24 holds the sum peak values, and the difference peak hold unit 25 holds the difference peak value.

On the other hand, the electrical signal processed by the high-pass filter 9b is also input to the rise detector 36 and the fall detector 37, and in a case where the rise R and the fall F are detected by the rise detector 36 and the fall detector 37, the detected signals are input to the pulse width acquisition unit 33, respectively. Then, in step S12, the pulse width acquisition unit 33 determines whether or not one of the rise R and the fall F is detected.

In a case where the pulse width acquisition unit 33 determines that one of the rise R and the fall F is detected, the pulse width acquiring unit 33 outputs a determination signal to the hold controller 22. Therefore, in a case where one of the rise R and the fall F is not detected, the pulse width acquisition unit 33 does not output a determination signal to the hold controller 22. At this time, in step S32, the hold controller 22 determines whether or not the hold time of the first timer 23 is equal to or larger than the predetermined pulse time.

The same as or similarly to Embodiment 2, the pulse time is preset based on the pulse width W of the pacing pulse P, and may be determined as, for example, 8 ms, which is a value larger than the pulse width W of the pacing pulse P.

In a case where the hold controller 22 determines that the hold time of the first timer 23 is equal to or larger than the pulse time, the hold controller 22 determines that the detected electrical pulse is a noise, proceeds to step S35, and stops and clears the first timer 23. The hold controller 22 stops and clears hold of the sum peak value of the sum peak hold unit 24 and the difference peak value of the difference peak hold unit 25, respectively. On the other hand, in a case where the hold controller 22 determines that the hold time of the first timer 23 is smaller than the pulse time, the hold controller 22 returns to step S12 to repeatedly determine whether or not one of the rise R and the fall F is detected by the pulse width acquisition unit 33.

In this way, the hold controller 22 is capable of easily controlling the sum peak hold unit 24 and the difference peak hold unit 25 based on the hold time of the first timer 23, and is capable of easily removing a noise.

In a case where, in step S12, the pulse width acquisition unit 33 determines that one of the rise R and the fall F is detected, for example, determines that the detected signal is input from the rise detector 36 and the rise R is detected, the same as or similarly to Embodiment 4, the pulse width acquisition unit 33 disables detection of the rise R by the rise detector 36 in step S13, and the timer controller 34 starts the second timer in step S14.

Subsequently, in step S15, the pulse width acquisition unit 33 determines whether or not the falling F is detected, and in a case where the falling F is detected, the pulse width acquisition unit 33 outputs the determination signal to the hold controller 22, and proceeds to step S16 to disables detection of the falling F by the fall detector 37. On the other hand, in a case where the pulse width acquisition unit 33 determines that the fall F is not detected, the pulse width acquisition unit 33 proceeds to step S17 to be processed in the same manner the same as or similarly to Embodiment 4.

When the pulse width acquisition unit 33 disables detection of the fall F in step S16, the pulse width acquisition unit 33 proceeds to step S18 to acquire the measurement time of the second timer 35, that is, the pulse width W, via the timer controller 34. The pulse width acquisition unit 33 outputs the acquired pulse width W to the pulse discrimination unit 51.

Here, when the determination signal output when the pulse width acquisition unit 33 determines that the fall F is detected is input to the hold controller 22, the hold controller 22 determines that the electrical pulse is detected, and outputs the sum peak value of the sum peak hold unit 24 and the difference peak value of the difference peak hold unit 25 to the comparison unit 12. Then, the comparison unit 12 compares the sum peak value with the difference peak value, and outputs the comparison result to the pulse discrimination unit 51.

In this way, when the pulse width W and the comparison result of the sum peak value and the difference peak value are input to the pulse discrimination unit 51, the pulse discrimination unit 51 determines whether or not the pulse width W is within a predetermined range in step S19.

In a case where the pulse discrimination unit 51 determines that the pulse width W is within the predetermined range, the pulse discrimination unit 51 proceeds to step S33 to determine whether or not the difference peak value is equal to or larger than the sum peak value based on the comparison result input from the comparison unit 12. On the other hand, in a case where the pulse discrimination unit 51 determines that the pulse width W falls out of the predetermined range, the pulse discrimination unit 51 proceeds to step S23 to determine that the electrical pulse is a noise.

In a case where the pulse discrimination unit 51 determines that the difference peak value is equal to or larger than the sum peak value in step S33, the pulse discrimination unit 51 proceeds to step S20 to determine the electrical pulse is the pacing pulse P. On the other hand, in a case where the difference peak value is smaller than the sum peak value, the pulse discrimination unit 51 proceeds to step S23 to determine the electrical pulse is a noise.

In this way, the pulse discrimination unit 51 discriminates based on the comparison result of the difference peak value and the sum peak value in addition to the pulse width W, and thus can discriminate the pacing pulses P with high accuracy.

In this way, when the pulse discrimination unit 51 determines that the electrical pulse is the pacing pulse P in step S20, or as a noise in step S23, the process proceeds to step S34, and the timer controller 34 stops and clears the second timer 35. Further, in step S35, the hold controller 22 stops and clears the first timer 23.

When the first timer 23 is cleared in step S35, the process returns to step S11, detection of the rising R and the falling F is enabled again, and the rise R and the fall F are repeatedly detected with respect to the sequentially input electrical signals.

According to the present embodiment, the pulse discrimination unit 51 discriminates based on the comparison result of the difference peak value and the sum peak value in addition to the pulse width W, and thus can discriminates the pacing pulses P included in the electrical signals with high accuracy.

In the above-described Embodiments 1 to 6, the electrodes 1a and 1b are detachably connected to the receiver 6, but are not limited thereto as long as they are electrically connected to the receiver 6. For example, the electrodes 1a and 1b may be integrally connected or wirelessly connected to the receiver 6.

In the above-described Embodiments 1 to 6, the electrodes 1a and 1b are disposed at two positions on the living body, but are not limited to two as long as they are capable of receiving electrical signals from a plurality of positions of the living body.

A pulse discrimination device relating to a first aspect of the presently disclosed subject matter is configured to receive electrical signals from a plurality of positions of a living body to which a pacing device for outputting a pacing pulse to cause a heart to beat is attached, and is configured to discriminate the pacing pulse included in the electrical signals. The pulse discrimination device includes: a differential processor configured to calculate a difference of the electrical signals received from the plurality of positions; a sum processor configured to calculate a sum of the electrical signals received from the plurality of positions; and a pulse discrimination unit configured to discriminate the pacing pulse included in the electrical signals based on the difference obtained by the differential processor and the sum obtained by the sum processor.

Here, the pulse discrimination device may further include a peak hold unit configured to hold a peak value of an absolute value with respect to the difference obtained by the differential processor as a difference peak value, and to hold a peak value of an absolute value with respect to the sum obtained by the sum processor as a sum peak value. The pulse discrimination unit may be configured to determine that the electrical signals received from the plurality of positions are the pacing pulse, in a case where the difference peak value held by the peak hold unit is equal to or larger than the sum peak value.

In addition, the pulse discrimination device my further include: a first timer configured to measure a hold time of the difference peak value and the sum peak value which are held by the peak hold unit; and a hold controller configured to clear the difference peak value and the sum peak value of the peak hold unit, in a case where the hold time of the first timer reaches a pulse time predetermined based on a time of a pulse width of the pacing pulse.

In addition, the pulse time may be set to a value larger than the time of the pulse width of the pacing pulse.

In addition, the pulse discrimination unit may be configured to determine that the electrical signals received from the plurality of positions are the pacing pulse, in a case where an absolute value of the difference is equal to or larger than an absolute value of the sum.

In addition, the pulse discrimination device may further include a pulse width acquisition unit configured to acquire a pulse width of the electrical signals received from the plurality of positions based on variation in an intensity of the electrical signals. The pulse discrimination unit may be configured to discriminate the pacing pulse further based on the pulse width acquired by the pulse width acquisition unit.

A pulse discrimination device relating to a second aspect of the presently disclosed subject matter is configured to receive electrical signals from a plurality of positions of a living body to which a pacing device for outputting a pacing pulse to cause a heart to beat is attached, and is configured to discriminate the pacing pulse included in the electrical signals. The pulse discrimination device includes: a pulse width acquisition unit configured to acquire a pulse width of the electrical signals received from the plurality of positions based on variation in an intensity of the electrical signals; and a pulse discrimination unit configured to discriminate the pacing pulse included in the electrical signals based on the pulse width acquired by the pulse width acquisition unit.

Here, the pulse discrimination may further include: a pulse detector configured to detect a rise and a fall of the electrical signals received from the plurality of positions; and a second timer configured to measure a time between the rise and the fall that are detected by the pulse detector. The pulse width acquisition unit may be configured to acquire the time between the rise and the fall, which is measured by the second timer as the pulse width.

In addition, the pulse discrimination device may further include a timer controller configured to start measurement of the second timer when one of the rise and the fall is detected by the pulse detector, and to stop and clear the measurement of the second timer when another one of the rise and the fall is detected by the pulse detector.

In addition, the timer controller may be configured to determine that an electrical pulse detected by the pulse detector is a noise, and to stop and clear a measurement time of the second timer, in a case where the measurement time of the second timer reaches a pulse time after the one of the rise and the fall is detected and before said another one of the rise and the fall is detected, the pulse time being predetermined based on a pulse width of the pacing pulse.

An electrocardiogram analyzer relating to a third aspect of the presently disclosed subject matter includes: the above-described pulse discrimination device; an electrocardiogram generator configured to generate an electrocardiogram based on an electrical signal received from a living body; and a display configured to display the electrocardiogram generated by the electrocardiogram generator.

According to the presently disclosed subject matter, since the pulse discrimination unit discriminates the pacing pulse included in the electrical signals based on the difference calculated by the differential processor and the sum calculated by the sum processor, it is possible to provide a pulse discrimination device and an electrocardiogram analyzer that discriminate a pacing pulse included in an electrical signal from a living body with high accuracy.

What is claimed is:

1. A pulse discrimination device configured to receive electrical signals from a plurality of positions of a living body to which a pacing device for outputting a pacing pulse to cause a heart to beat is attached, the pulse discrimination device comprising:
   a timer;
   at least one processor and memory collectively configured to:
      detect a rise and a fall of a pulse in the electrical signals;
      cause the timer to start a measurement when one of the rise and the fall is detected, and to cause the timer to stop the measurement of the timer when another one of the rise and the fall is detected, a time between the start and stop of the measurement being a pulse width of the detected pulse;
      compare the pulse width to a predetermined range;
      determine the pulse as being from the pacing pulse included in the electrical signals when the pulse width is within the predetermined range, and determine the pulse as noise or from an electrocardiogram signal when the pulse width is not within the predetermined range; and
      stop detecting the rise and the fall in the electrical signals until a predetermined time passes since a last detected pacing pulse,
   wherein the predetermined time is greater than the pulse width and is less than a time interval at which the pacing pulse is output from the pacing device, and
   wherein the electrical signals comprise the pacing pulse and the electrocardiogram signal.

2. The pulse discrimination device according to claim 1, wherein the at least one processor and memory are further collectively configured to determine that the detected pulse is a noise, and to stop and clear a measurement time of the timer, when a measured time is greater than the predetermined pulse time after the one of the rise and the fall is detected and before said another one of the rise and the fall is detected.

* * * * *